United States Patent [19]

Sasaki et al.

[11] Patent Number: 4,939,091
[45] Date of Patent: Jul. 3, 1990

[54] NOVEL AUEROBASIDIUM SP. MICROORGANISMS, METHOD FOR OBTAINING THE SAME AND METHOD FOR PREPARING ERYTHRITOL WITH THE SAME

[75] Inventors: Takashi Sasaki; Takafumi Kasumi; Naoya Kubo; Keiji Kainuma, all of Sakura; Katsuo Wako, Gyoda; Hiroaki Ishizuka, Yatabe; Gaku Kawaguchi, Gyoda; Tsunero Oda, Akikawa, all of Japan

[73] Assignees: Director of National Food Research Institute, Ministry of Agriculture, Forestry and Fisheries, Ibaraki; Nikken Chemicals Co., Ltd., Tokyo, both of Japan

[21] Appl. No.: 88,858

[22] Filed: Aug. 24, 1987

[30] Foreign Application Priority Data

Sep. 9, 1986 [JP] Japan ................................. 61-210669
Feb. 6, 1987 [JP] Japan ................................. 62-024716

[51] Int. Cl.$^5$ ......................... C12P 7/18; C12P 1/645; C12N 1/20; C12R 1/01
[52] U.S. Cl. .................................... 435/158; 435/171; 435/172.1; 435/911
[58] Field of Search ...................... 435/822, 158, 170.1, 435/911, 172.1, 170, 171

[56] References Cited

U.S. PATENT DOCUMENTS 2,986,495 5/1961 Onishi .................................. 435/158
3,756,917 9/1973 Dezeeuw et al. .................... 435/158

FOREIGN PATENT DOCUMENTS 0136802  4/1984  European Pat. Off. ............ 435/158
0136804  4/1985  European Pat. Off. ............ 435/158
0136805  4/1985  European Pat. Off. ............ 435/158
0003546  6/1962  Japan ................................. 435/158
0041549 10/1972  Japan ................................. 435/158
0118889 11/1974  Japan ................................. 435/158
1031080  2/1986  Japan ................................. 435/158
1031082  2/1986  Japan ................................. 435/158
1031091  2/1986  Japan ................................. 435/158
2096090  5/1987  Japan ................................. 435/158
 824184 11/1959  United Kingdom ................ 435/158

Primary Examiner—Herbert J. Lilling
Attorney, Agent, or Firm—Frishauf, Holtz, Goodman & Woodward

[57] ABSTRACT

Biologically pure culture of Aureobasidium sp. SN-124A strain (FERM BP-1429) and artificial mutants thereof according to the present invention show the properties of forming and accumulating erythritol in a culture solution, when aerobically cultured on a liquid culture medium containing an assimilable carbon source and an assimilable nitrogen source, and are useful for the preparation of erythritol by fermentation of sugars. A method for preparing erythritol by fermentation of sugars according to the present invention comprises inoculating microorganism selected from the group consisting of Aureobasidium sp. SN-124A strain (FERM BP-1429) and mutants thereof on a liquid culture medium of pH 4 to 9 containing an assimilable carbon source and an assimilable nitrogen source, and aerobically culturing them at a temperature of 30° to 38° C. to form and accumulate erythritol in said culture medium for collection.

8 Claims, No Drawings

NOVEL AUEROBASIDIUM SP. MICROORGANISMS, METHOD FOR OBTAINING THE SAME AND METHOD FOR PREPARING ERYTHRITOL WITH THE SAME

BACKGROUND OF THE INVENTION

The present invention relates to novel microorganism, a method for obtaining the same, and a method for preparing erythritol by fermentation, using the same. More specifically, the present invention relates to *Aureobasidium* sp. SN-124A strain and its artificial mutants, *Aureobasidium* sp. SN-G42 and SN-γ96, a method for obtaining such microorganisms, and a method for preparing erythritol by converting fermentable sugars to erythritol with said microorganisms.

It is well-known to prepare erythritol by fermentation, using microorganisms. The microorganisms so far known to be capable of producing erythritol include, for instance, those belonging to *Debaryomyces* sp. (U.S. Pat. No. 2,986.495), *Pichia* sp. (U.S. Pat. No. 2,986,495), *Candida* sp. (U.S. Pat. No. 3,756,917), *Moniliella* sp. (Antonie van Leeuwenhoek, 37(1971)107-118 and such), *Aureobasidium* sp. (Japanese Patent Laid-Open Publication No. 61-31091) and the like.

However, such known microorganisms have not still been used on an industrial scale due to their grave disadvantage that cannot practically be neglected.

More exactly, U.S. Patent NO. 2,986,495 discloses a method for preparing arabitol, glycerol and erythritol from monosaccharides with the use of *Pichia* sp. and *Debaryomyces* sp. microorganisms. According to this method, however, only a small amount of erythritol may be produced as the byproduct, which should be separated out and collected with considerable difficulty.

U.S. Pat. No. 3,756,917 teaches a method for the preparation of erythritol from hydrocarbons using *Canadian* sp. microorganisms. However, this method is of low productivity and so uneconomical due to the need that the substrate concentration be at most 20 %. Another disadvantage is that the product cannot be used for foods, since there is a likelihood that the starting hydrocarbons may remain in the product.

Antonie van Leeuwenhoek, 37, 107-118 (1971) and Applied Microbiology, 12, [3]240-246 (1964) describes a method for preparing erythritol from glucose with the use of *Moniliella* (Torula) sp. microorganisms. This method is characterized in that the ratio of conversion of glucose to erythritol is high and the substrate concentration of a culture media may be increased to a relatively high level, but has the disadvantage that a large amount of xanthane gum should be used for defoaming, since marked foaming occurs at the time of culture.

Japanese Patent Laid-Open Publication No. 61-31091 describes methods for preparing erythritol from monosaccharides with the use of *Aureobasidium* sp. microorganisms. These methods make it possible to prepare erythritol using a relatively high substrate concentration of a culture media and, hence, are valuable in its own way.

However, these methods are not always satisfactory owing to the disadvantages that the yield of erythritol are not only unsatisfactory relative to the amount of cells grown by microorganisms, but the optimum pH, temperature and the like are also harrow, and, even if such factors depart slightly from the optimum ranges, there is then a remarkable drop of the yield of erythritol.

As a result of screening performed in view of the aforesaid considerations and on the erythritol productivity of many microorganisms in order to obtain erythritol-producing microorganisms of high industrial significance, it has been found that novel microorganisms belong to *Aureobasidium* sp. and isolated from a soil within a starch plant in Okinawa Prefecture, Japan, show high erythritol productivity.

SUMMARY OF THE INVENTION

Therefore, a basic object of the present invention is to provide novel microorganisms which show high erythritol productivity and is of high industrial significance.

Another object of the present inveniton is to provide microorganisms which can keep high erythritol productivity even in a culture media of high concentration.

A further object of the present invention is to provide microorganisms which can produce highly hydrophilic cells with no occurrence of foaming during culture.

A still further object of the present invention is to provide methods for obtaining such useful microorganisms as mentioned above.

A still further object of the present invention is to provide methods for efficiently preparing erythritol with the use of such microorganisms as mentioned above.

Other objects of the present invention will become apparent from the following detailed description.

According to the present invention, the aforesaid objects of the present invention are achieved by wild-type *Aureobasidium* sp. SN-124A strain and SN-G42 and SN-γ96 mutants obtained by artificial mutation of such SN-124A strain. Further, the aforesaid objects of the present invention are achieved by inoculating said strains on a culture media containing fermentable sugars, and aerobically culturing them to accumulate erythritol in a culture solution, followed by collection thereof.

DETAILED DESCRIPTION OF THE INVENTION

The inventive microorganism *Aureobasidium* sp. SN-124A strain was purified and isolated by the present inventors from the soil within a starch plant in Okinawa Prefecture, Japan, in the conventional manner (Applied Microbiology 12[1]87 (1964), Can. J. Microbiol. 2, 72 (1956)). The vegetative cells take on a unicellular or egg-form shape, and are propagated by multipolar budding with no formation of any ascospore, and the mycelia form true hyphae with a number of multi-lateral budding type conidia occurring at the tip and sides. The strains grow rapidly on a YM agar culture medium so that a white colony turns to a black colony within 3 days, form a film in liquid culture, and are capable of converting fermentable sugars to the main product erythritol and a small amount of glycerol.

The inventive microorganisms *Aureobasidium* sp. SN-G42 and *Aureobasidium* sp. SN-γ96 strains were prepared by irradiating and treating said *Aureobasidium* sp. SN-124A strain (parent strain) with ultraviolet rays and a mutagenic agent, and further irradiating them with gamma rays, if desired.

The method for obtaining such mutants will now be explained. SN-124A strain is aerobically cultured on a liquid culture medium having a glucose concentration of 22 % to obtain a cultured product, which is then irradiated with ultraviolet rays for a given period of time. Thereafter, the cultured product is applied over and cultured on an agar culture medium having a glucose concentration of 22 % to pick up grown strains. The thus picked-up strains are aerobically cultured on a liquid culture medium having a glucose concentration of 33.5 % to separate the cells, which are in turn treated with an 1 mg/m( concentration of N-methyl-N'-nitro-N-nitrosoguanidine in a buffer solution. Subsequently, the thus treated product (cells) is applied over and cultured on an agar culture medium having a glucose concentration of 40 % to pick up grown strains and thereby obtain *Aureobasidium* sp. SN-G42 strain.

Next, the thus picked-up strain is aerobically cultured in a liquid culture medium having a glucose concentration of 40 %, and the cultured product is irradiated with a given dose of Co gamma rays. Thereafter, the treated cells are applied over and cultured on an agar culture medium having a glucose concentration of 45 %, and the grown strains are picked up as *Aureobasidium* sp. SN-γ96 strain. Since the thus prepared mutants *Aureobasidium* sp. SN-G42 and SN-γ96 have a rate of conversion to erythritol higher than that of the parent strain (wild-type) *Aureobasidium* sp. SN-124A strain, excel in the tolerance of high sugars concentration and produce hydrophilic cells, they are further preferred for the industrial production of erythritol.

The *Aureobasidium* sp. SN-124A strain used in the present invention have the following mycological properties.

1. State of Growth on Culture Media (1) Microscopic Examination
Size of Vegetative Cells (*1) : 4–7×4–15 microns.
Shape of Vegetative Cells (*1) : Hypha- or Yeast-like unicellular or egg-shape.
Propagation of Vegetative Cells (*1) : Hypha or Multipolar budding of yeast-like cells.
Mycelia (*2) : Mycelia form true hyphae with a number of multi-lateral budding type conidia occurring at the tip and sides.
Note *1 : Cultured on a YM agar culture medium at 27° C. for 5 days.
*2 : Slide culture by potato glucose agar.

(2) Agar Slant (*3)
Growth : Satisfactory.
Gloss : Not observed.
Color Tone: The colony turns from white to black with the lapse of time.
Note *3 : YM agar culture medium.

(3) Liquid Culture (*4)
Surface Growth : Formation of thick film.
Degree of Turbidity : Transparence.
Grust : Marked.
Note *4 : YM liquid culture medium

2. Formation of Ascospore
Potato glucose agar culture medium : Not formed.
Corn meal agar culture medium : Not formed.
YM agar culture medium : Not formed.
Carrot extract culture medium : Not formed.
$V_s$ culture medium : Not formed.

3. Physiological Properties
Oxygen Demand : Aerobic.
Growth Temperature : Up to about 40° C.
Optimum Growth Temperature : 35 to 37° C.
Growth pH : 2.5 to 9.5.
Optimum Growth pH : 4 to 7.
$KNO_3$ Assimilation (*5) : Found.
$(NH_4)_2SO_4$ Assimilation (*5) : Found.
Decomposition of Urea : Found.
Liquefication of Gelatine : Not found.
Formation of Carotenoid : Not found.
Formation of Organic Acids : Found.
Albutin : Not found.
Formation of Starchy Substances : Not found.
Vitamin Demand (*5) : Found.
Glucose Concentration (*6) : 50 % Growth + +. 60 % Growth + +.
Salt Concentration (*7) : 2 % Growth +. 6 % Growth —.
Note *5 : Estimated by the method of J. Lodder et al in which a Wickerham's synthetic medium was used.
*6 : Agar Medium
*7 : Liquid Medium

4. Fermentability of Sugars (*5)
Glucose + +
Lactose —
Galactose —
Melibiose —
Sucrose + +
Raffinose —
Maltose +
Cellobiose —
Trehalose —
Inulin —

5. Assimilation of Sugars, Organic Acids and so on
Glucose + +
D-Xylose ±
Galactose —
Erythritol +
D-Arabinose —
L-Arabinose —
D-Ribose +
Sucrose +
L-Rhamnose —
Maltose +
Ethanol —
Cellobiose +
Salicin —
L-Sorbose —
Ribitol —
Galactitol —
Glycerol +
Trehalose —
Lactose —
Melibiose —
D-Mannitol +
Raffinose —
Melezitose —
α-Methyl-D-Glucoside —
Inulin ±
Inositol —
Soluble Starch —
DL-Lactic Acid —
Succinic Acid ±
Citric Acid +

As a result of investigations made of the taxonomical position of the present strains having such mycological properties as mentioned above, referring to the Genera of Fungi Sporulating in Pure Culture (J. A. Von Arx; 1974), it has been found that the present strains are characterized by forming a colony turning from white to black with the lapse of time at the later stage of culture on a YM agar medium, forming mycelia on vegetative cells, giving rise to a number of blast spores without any thick sporulation, and so on. Thus, the present strains have been judged to be novel microorganisms belonging to the genus *Aureobasidium*, and named *Aureobasidium* sp. SN-124A strain.

On the other hand, the mycological properties of *Aureobasidium* sp. SN-G42 and SN-γ96 strains bear very close resemblance to those of the aforesaid parent *Aureobasidium* sp. SN-124A strain (wild-type). In other words, the mutants have the same mycological properties as those of the parent strain, except that the former gives rise to a colony which is wrinkled on the surface when cultured on an agar culture medium, show slight reduced assimilation of nitrates and are unable to decompose urea, and that the former is somewhat different from the latter in the "Assimilation of Sugars, Organic Acids and so on" as set forth in Table 1.

TABLE 1

| Substrate | Assimilation of Sugars, Organic Acids and so on | | |
|---|---|---|---|
| | SN-124A | SN-G42 | SN-96 |
| Glucose | ++ | + | + |
| D-Xylose | ± | − | − |
| L-Sorbose | − | + | + |
| D-Mannitol | + | − | − |
| Raffinose | − | + | + |
| Melezitose | − | + | + |
| Inulin | ± | + | + |
| Succinic Acid | ± | − | − |
| Citric Acid | ± | − | − |

As can clearly be seen from the foregoing explanation, *Aureobasidium* sp. SN-G42 and SN-γ96, that are the mutants, have the mycological properties bearing very close resemblance to those of *Aureobasidium* sp. SN-124A strain that is the parent strain (wild-type). As will be illustrated in the examples to be given later, however, these mutants are different from the parent, *Aureobasidium* sp. SN-124A strain in that the higher tolerance of sugars concentration, and the cells are so hydrophilic that any foaming does not substantially occur during culture.

More specifically, *Aureobasidium* sp. SN-124A strain (wild-type) shows a relatively satisfactory conversion ratio to erythritol of about 37.0 to 41.5 % under the condition that the glucose concentration of a culture media are up to 33.5 %. However, there is a sharp drop of the convertion ratio to erythritol at a glucose concentration exceeding 39.5 %. At a glucose concentration of 45 %, that conversion decreases to about 16 %. With *Aureobasidium* sp. SN-G42 and SN-γ96 strains, on the other hand, the conversion ratio to erythritol does not virtually drop, even when the glucose concentration of a culture medium exceeds 40 %. At a glucose concentration of as high as 45 %, a satisfactory conversion ratio is attained. Particularly with SN-γ96 strain, a high conversion ratio higher than 40 % is maintained, even when the glucose concentration of a culture medium exceeds 60 %, and a conversion ratio of as high as 32 % is attained, even when the glucose concentration of a culture medium is 75 %. Further, SN-γ96 and SN-G42 strains are characterized in that their cells are so hydrophilic that any foaming does not substantially occur during culture.

The strains according to the present invention have been deposited with Fermentation Research Institution of Agency of Industrial Science and Technology under FERM P-8745 (FERM BP-1429) for *Aureobasidium* sp. SN-124A strain, FERM P-8940 (FERM BP-1430) for *Aureobasidium* sp. SN-G42 and FERM P-9400 (FERM BP-1431) for *Aureobasidium* sp. SN-γ96.

In what follows, the methods for preparing erythritol using the microorganisms according to the present invention will be explained. In the specification, it is to be understood that % shall means w/v %, unless otherwise noted.

The present strains are cultured under aerobic conditions on a liquid culture medium containing an assimilable carbon source, in assimirable nitrogen source, inorganic salts and the like.

For the carbon source of the liquid culture media, use may be made of fermentable sugars such as glucose, fructose and sucrose. The upper limit of the sugar concentration varies depending upon the strains used and, hence, is not generally determined. However, a sugar concentration of preferably 10 to 40 %, more preferably 20 to 30 % is used with SN-124A strain. With SN-G42 strain, a sugar concentration of 10 to 55 %, preferably 20 to 50 % is applied, and with SN-γ96 strain, a sugar concentration of 10 to 95 %, preferably 0 to 70 % is used.

As the nitrogen sources, nitrogen compounds available by miroorganisms are used such as, for instance, yeast extract, malt extract, casamino acids, corn steep liquor, ammonium sulfate and urea. These nitrogen sources are preferably used in an amount of 0.5 to 3.0 % for yeast extract, and 1.5 to 10 % for corn steep liquor.

The inorganic salts used include salts such as ferrous sulfate, sodium chloride, dipotassium hydrogen phosphate, calcium hydroxide and zinc sulfate, and are preferably used in an amount not more than 0.1 %.

It is to be noted that in addition to these carbon sources, nitrogen sources and inorganic salts, various organics and inorganics required for the growth of microorganisms or conventionally used defoamers or the like may be added.

For culture, the cells of the present microorganisms may be inoculated directly on the liquid culture media having the aforesaid composition, or a separate seed culture solution obtained by pre-culture may be inoculated thereon. Such a seed culture solution is prepared by the inoculation of a loopfull of yeast-like slant-cultured in the conventional manner on a liquid culture media of pH 4 to 7 containing 40.0 % of glucose and 1.6 % of yeast extract, followed by culture at 34 to 37° C. for 2 to 4 days.

Culture is carried out in a temperature range in which microorganisms can grow, i.e., at 30 to 38° C, preferably 35 to 37° C.

The culture media are adjusted to pH 4 to 9, preferably 4 to 7.

The culture period varies depending upon the type of the media used and the concentration of sugar that provides the carbon source, but is usually about 4 to 15 days. Referring to the mode of culture, it may be carried out either batchwise or continuously.

It is desired that the most use be made of the nutrition source of the culture media, and culture come to an end at the time when the amount of erythritol produced in the culture solution reaches a maximum. For that purpose, it is desired that culture be carried out, while measuring the amount of erythritol in the culture solution by means of the known methods such as GLC (gas liquid chromatography) and HPLC (high performance liquid chromatography).

Erythritol accumulated in the culture solution may be separated therefrom in the conventional manner after the completion of culture. To this end, use may be made of the known means ordinarily employed in the art such as filtration, centrifugation, ion exchange or adsorption chromatography, solvent extraction, distillation and crystallization which may suitably be combined, if required. By way of example, the cells are removed from the culture solution as by filtration or centrifugation, and the obtained solution is treated with activated charcoal to remove colored matters. Then, that solution is further deionized with an ion exchange resin, and is thereafter concentrated into a syrup, from which erythritol is finally separated by crystallization.

The invented novel microorganisms SN-124A strain belonging to the genus *Aureobasidium* and the mutants, *Aureobasidium* sp. SN-G42 and *Aureobasidium* sp. SN-γ96 show a high erythritol conversion ratio from sugars and are thus suitable for industrial use. In particular, the mutants SN-G42 and SN-γ96 are extremely useful for the industrial purpose, since they have considerably high tolerance to sugars concentration, excel in heat resistance, and give rise to no substantial foaming, when cultured.

The embodiments of the present invention will now be explained further concretely with reference to the following examples.

Example 1

(a) Preparation of Seed Culture Solution

The cells of Aureobasidium sp. SN-124A strain (FERM BP-1429 were applied over a slant culture medium comprising 20.0 % (w/w) of glucose, 0.5 % of yeast extract and 1.5 % of agar, and stationary culture was carried out at 35° C. for 3 days.

Then, one platinum loop of the aforesaid cultured cells was transplanted into a Erlenmeyer flask having a volume of 500 m( loaded therein with 100 m( of a liquid culture medium (pH 5.5) containing 20 % (w/w) of glucose and 2.0 % of corn steep liquor (manufactured by Oji Corn Starch Co., Ltd.); and cultivation was carried out at 35° C. for 3 days to obtain a cultured product.

(b) Main Culture

Five (5) kg of a culture medium containing 20 (w/w) of glucose, 2.0 % of corn steep liquor preadjusted to pH 6.0, 0.1 % of sorbitan fatty acid ester and 0.03 % of a silicon base defoamer were put in a fementer having a volume of 7 (, and were then sterilized at 120° C. for 20 minutes. After cooled off, pH of the medium was adjusted to 5.5. Added to this were 200 m( of a seed culture solution of *Aureobasidium* sp. SN-124A strain (FERM P-8745, FERM BP-1429) prepared in the aforesaid step (a). That medium was cultured at 35° C. and 400 rpm under an aeration of 1 l/min. for 7 days. As a result, 467 g of erythritol and a trace of glycerol were built up in this culture solution.

The cells were centrifuged from the culture solution, which was in turn decolored with activated charcoal and desalted with an ion exchange resin (IRA-410: IRA-120B =2 : 1), and was then concentrated and stored at 5° C. to obtain crystals. The crystals were dissolved and recrystallized in a similar manner. The obtained polyhedral white crystals were of a delightful sweet taste and had a melting point of 121° C. From the results of NMR, the specific optical rotation, HPLC and GLC, the white crystals were indentified as erythritol (meso-erythritol).

Example 2

Fifty (50) g of a medium containing 30 % (w/w) of glucose and 3.2 % of corn steep liquor (adjusted to pH 6.0) were put in a 500 m( Erlenmyer flask, followed by sterilization and cooling. Thereafter, the medium was adjusted to pH 6.0. Inoculated on this were 2 ml of a seed culture solutuion similar to that used in Ex. 1 for 10-day rotary shaking culture at 35° C. and 180 rpm. As a result, 5.9 g of erythritol and 1.4 g of glycerol were accumulated in broth.

Example 3

Fifty (50) g of a culture medium containing 20 % (w/w) of sucrose and 0.5 % of yeast extract were put in a 500 m( Erlenmyer flask, and were sterilized at 120° C. for 15 minutes. After cooling, the medium was adjusted to pH 6.0, and was inocualted with *Aureobasidium* sp. SN-124A strain (FERM BP-1429) for rotary shaking culture at 35° C. and 180 rpm for 7 days. As a results, 4.2 g of erythritol were accumulated in the culture solution, but any accumulation of glycerol was not found.

Example 4

Fifty (50) g of a culture medium containing 0.5 % of yeast extract and 10 to 30 % (w/w) of glucose were put in 500 ml Erlenmyer flasks, and were sterilized at 120° C. for 15 minutes. After cooling, the media were adjusted to pH 5.5, and were inoculated with 2 ml of a seed culture solution (obtained by culturing *Aureobasidium* sp. SN-124A strain (FERM BP-1249) on a culture medium comprising 20 % of glucose and 0.5 % of yeast extract at 35° C. for 3 days for rotary shaking culture) at 35° C. and 180 rpm for 4 to 11 days. The results were as set forth in Table 1.

TABLE 1

| Glucose Concentration (%) | Culture Periods (days) | Yields* (%) Erythritol | Glycerol | Glucose Residues (%) |
|---|---|---|---|---|
| 10 | 4 | 40.6 | 1.0 | 0 |
| 15 | 6 | 41.8 | 2.6 | 0 |
| 20 | 7 | 46.2 | 3.4 | 2.2 |
| 25 | 9 | 42.2 | 7.8 | 15.7 |
| 30 | 11 | 37.0 | 10.6 | 23.3 |

*per consumed glucose

Example 5

Fifty (50) g of a culture medium comprising 20 % (w/w) of glucose and 0.5 % of yeast extract were put in each of eight 500 m( Erlenmyer flasks, and were sterilized. After cooling, the medium was adjusted to pH range of 2.9 to 10.1 with 1 N hydrochloric acid or 1 N sodium hydroxide. Each of the obtained media was then inoculated with seed strains (*Aureobasidium* sp. SN-124A strain,- FERM BP-1429) for 7-day rotary shaking culture at 35° C. and 180 rpm. As a result, erythritol was obtained in the yields as set forth in Table 2.

TABLE 2

| pH of Culture Media | Yields* (%) Erythritol | Glycerol | Glucose Residues (%) |
|---|---|---|---|
| 2.9 | 35.8 | 6.4 | 27.5 |
| 4.1 | 42.0 | 8.1 | 14.0 |
| 5.1 | 46.6 | 9.2 | 16.1 |
| 6.1 | 45.6 | 7.2 | 12.8 |
| 6.7 | 46.2 | 8.0 | 15.0 |
| 7.8 | 47.2 | 5.0 | 23.0 |
| 9.1 | 41.6 | 3.0 | 35.7 |
| 10.1 | 1.0 | 0 | 81.9 |

*per consumed glucose

Example 6 (Preparation of Mutents)

*Aureobasidium* sp. SN-124A strain (FERM BP-1429) was precultured on a culture medium containing 0.5 % of yeast extract and 22 % of glucose for 2 days. The pre-cultured product was diluted 100-fold, and was irradiated with a 15-W ultraviolet lamp (Toshiba Sterilizer Lamp GL15) from a distance of 30 cm for 40 minutes. After dilution, the irradiated product was applied over an agar culture medium (1.0 % of yeast extract, 33.5 % of glucose and 1.5 % of agar) to pick up growing strains.

The thus picked-up strain was again irradiated with ultraviolet rays to pick up growing strains in a similar manner.

Further, the thus picked-up strain was treated with an 1 mg/ml concentration of N-methyl-N'-nitro-N''-nitrosoguanidine for 30 minutes to pick up growing strains in a similar manner and thereby obtain *Auroebasidium* sp. SN-G42 strain (FERM P-8940, FERM BP-1430) which was the mutant.

Example 7

(a) Preparation of Seed Culture Solution

The cells of Aureobasidium sp. SN-G42 strain (FERM BP-1430) were applied over a slant culture medium comprising 33.5 % of glucose, 1.0 % of yeast extract and 1.5 % of agar, and stationary culture was carried out at 35° C. for 2 to 3 days.

Then, a loopfull of the aforesaid cultured cells was transplanted into an Erlenmeyer flask having a volume of 500 m( loaded therein with 150 ml of a liquid culture medium (pH 4.0) containing 20 % of glucose and 1.6 % of corn steep liquor (manufactured by Oji Corn Starch Co., Ltd.), and cultivation was carried out at 35° C. for 3 days. Further, 9 ml of this culture solution were inoculated into a 500 ml Erlenmeyer flask loaded therein with 150 ml of a similar liquid culture medium, and rotary shaking culture was carried out at 35° C. for 3 days.

(b) Main Culture

Fifteen (15)l of a culture medium containing 20.0 % of glucose and 1.6 % of corn steep liquor were put in a fermeter of 30 ( in volume, to which 300ppm of a deformer (Silicone KS-66 manufactured by Shinetsu Kagaku, Co., Ltd.) were then added, followed by steam sterilization at 120° C. for 20 minutes. After cooling, the culture medium was adjusted to pH 4.0 with caustic soda. Added to this medium were thereafter 6 % of the seed culture solution of *Aureobasidium* sp. SN-G42 strain (FERM BP-1430). Culture was then carried out at 35° C. and 230 rpm under an aeration of 0.25 vvm.

After the completion of culture, the analysis of the culture solution indicated that the glycerol was entirely consumed, and the yields of erythritol and glycerin therein were 49.3 % and 2.2 %, respectively.

Next, a part of this culture solution was freed of the cells by centrifugation, and was further decolored and desalted with activated charcoal and an ion exchange resin (IRA-410 : IR-120B =2 : 1). The resulting liquid was concentrated to a sugar concentration of at least 50 %, and was slowly cooled to obtain crystals, which were in turn dissolved in water and recrystallized in a similar manner.

The thus obtained polyhedral white crystals were of a comfortable sweet taste, and had a melting point of 121° C. From the results of HPLC and GLC and the measurement of the optical rotation and nuclear magnetic resonance spectra, the aforesaid crystals were identified as erythritol (meso-erythritol).

Example 8

Fifteen (15) ( of a culture medium containing 20.0 % of glucose and 1.6 % of corn steep liquor were loaded into a fermenter of 30 ( in volume, and were added with 300 ppm of a defoamer, followed by steam sterilization at 120° C. for 20 minutes. After cooling, the culture medium was adjusted to pH 4.0 with caustic soda. Added to this medium was thereafter 6 % of a seed culture solution of *Aureobasidium* sp. SN-G42 strain (FERM BP-1430) prepared with the same medium as the aforesaid medium in accordance with the procedures of Example 7. Cultivation was then carried out at 35° C. and 230 rpm under an aeration of 0.50 vvm for 7 days.

After the completion of cultivation, the analysis of the culture solution indicated that the glucose was entirely consumed, and the yields of erythritol and glycerol therein were 49.2 % and 1.2 %, respectively.

Example 9

Fifteen (15) l of a culture medium containing 20.0 % of glucose and 1.6 % of corn steep liquor were loaded into a fermenter of 30 ( in volume, and were added with 300 ppm of a defoamer, followed by steam sterilization at 120° C. for 20 minites. After cooling, pH of the culture medium was adjusted to 4.0 with caustic soda. Added to this medium was thereafter 6 % of a seed culture solution of *Aureobasidium* sp. SN-G42 strain (FERM BP-1430) prepared with the same medium as the aforesaid medium in accordance with the procedures of Example 7. Culture was then carried out at 35° C. and 30 rpm under an aeration of 0.75 vvm for 7 days.

After the completion of culture, the analysis of the culture solution indicated that the glucose was entirely consumed, and the yields of erythritol and glycerol therein were 46.5 % and 2.7 %, respectively.

Example 10

Fifteen (15) ( of a culture medium containing 20.0 % of glucose and 1.6 % of corn steep liquor were loaded into a fermenter of 30 ( in volume, and were added with 300 ppm of a defoamer, followed by steam sterilization at 120° C. for 20 minutes. After cooling, the culture medium was adjusted to pH 4.0 with caustic soda. Added to this medium was thereafter 900 ml of a seed culture solution of *Aureobasidium* sp. SN-G42 strain (FERM BP-1430) prepared with the same medium as the aforesaid medium in accordance with the procedures of Example 7. Culture was then carried out at 35° C. and 230 rpm under an aeration of 1.00 vvm for 7 days.

After the completion of culture, the analysis of the culture solution indicated that the glucose was entirely consumed, and the yields of erythritol and glycerol therein were 41.8 % and 1.4 %, respectively. Example 11

Five (5) ( of a culture medium containing 33.5 % of glucose and 4.47 % of corn steep liquor were loaded into a fermenter of 7 l in volume, and were added with 300 ppm of a defoamer, followed by steam sterilization at 120° C. for 20 minutes. After cooling, the culture medium was adjusted to pH 4.2 with caustic soda. Added to this medium was thereafter 300 ml of a seed culture solution of *Aureobasidium* sp. SN-G42 strain (FERM BP-1430) prepared with the same medium as the aforesaid medium in accordance with the procedures of Example 7. Culture was then carried out at 35° C. and 500 rpm under an aeration of 0.25 vvm for 5 days.

After the completion of culture, the analysis of the culture solution indicated that the glucose was entirely consumed, and the yields of erythritol and glycerol therein were 39.7 % and 7.9 %, respectively.

Example 12

Five (5) l of a culture medium containing 39.5 % of glucose and 4.0 % of corn steep liquor were loaded into a fermenter of 7 ( in volume, and were added with 300 ppm of a defoamer, followed by steam sterilization at 120° C. for 20 minutes. After cooling, the culture medium was adjusted to pH 4.2 with caustic soda. Added to this medium was thereafter 300 ml of a seed culture solution of *Aureobasidium* sp. SN-G42 strain (FERM BP-1430) prepared with the same medium as the aforesaid medium in accordance with the procedures Example 7. Culture was then carried out at 35° C. and 500 rpm under an aeration of 0.25 vvm for 6 days.

After the completion of culture, the analysis of the culture solution indicated that glucose was entirely consumed, and the yields of erythritol and glycerol therein were 38.6 % and 9.5 %, respectively.

Example 13

Five (5) l of a culture medium containing 39.5 of glucose and 5.3 % of corn steep liquor were loaded into a fermenter of 7 ( in volume, and were added with 300 ppm of a defoamer, followed by steam sterilization at 120° C. for 20 minites. After cooling, the culture medium was adjusted to pH 4.2 with caustic soda. Added to this medium was thereafter 300 ml of a seed culture solution of *Aureobasidium* sp. SN-G42 strain (FERM BP-1430) prepared with the same medium as the aforesaid medium in accordance with the procedures of Example 7. Culture was then arried out at 35° C. and 500 rpm under an aeration of 0.25 vvm for 5 days.

After the completion of culture, the analysis of the culture solution indicated that the glucose was entirely consumed, and the yields of erythritol and glycerol therein were 37.5 % and 7.2 %, respectively.

Example 14

Five (5) l of a culture medium containing 39.5 % of glucose and 6.6 % of corn steep liquor were loaded into a fermenter of 7 ( in volume, and were added with 300 ppm of a defoamer, followed by steam sterilization at 120° C. for 20 minutes. After cooling, the culture medium was adjusted to pH 4.2 with caustic soda. Added to this medium was thereafter 300 ml of a seed culture solution of *Aureobasidium* sp. SN-G42 strain (FERM BP-1430) prepared with the same medium as the aforesaid medium in accordance with the procedures of Example 7. Culture was then carried out at 35° C. and 500 rpm under an aeration of 0.25 vvm for 4 days.

After the completion of culture, the analysis of the culture solution indicated that the glucose was entirely consumed, and the yields of erythritol and glycerol therein were 37.1 % and 4.8 %, respectively.

Example 15

Fifteen (15) ( of a culture medium containing 45.0 % of glucose and 6.0 % of corn steep liquor were loaded into a fermenter of 30 ( in volume, and were added with 300 ppm of a defoamer, followed by steam sterilization at 120° C. for 20 minutes. After cooling, the culture medium was adjusted to pH 4.0 with caustic soda. Added to this medium was thereafter 6 % of a seed culture solution of *Aureobasidium* sp. SN-G42 strain (FERM BP-1430) prepared with the same medium as the aforesaid medium in accordance with the procedures of Example 7. Culture was then carried out at 35° C. and 230 rpm under an aeration of 0.33 vvm for 8 days.

After the completion of culture, the analysis of the culture solution indicated that the glucose was entirely consumed, and the yields of erythritol and glycerol therein were 37.3 % and 4.5 %, respectively.

Example 16

Five (5) ( of a culture medium containing 33.5 % of sucrose and 4.5 % of corn steep liquor were loaded into a fermenter of 7 ( in volume, and were added with 300 ppm of a defoamer, followed by steam sterilization at 120° C. for 20 minutes. After cooling, the culture medium was adjusted to pH 4.1 with caustic soda. Added to this medium was thereafter 300 ml of a seed culture solution of *Aureobasidium* sp. SN-G42 strain (FERM BP-1430) prepared with the same medium as the aforesaid medium in accordance with the procedures of Example 7. Culture was then carried out at 35° C. and 500 rpm under an aeration of 0.25 vvm for 6 days.

After the completion of culture, the analysis of the culture solution indicated that the sucrose was entirely consumed, and the yields of erythritol and glycerol therein were 41.9 % and 7.4 %, respectively.

Example 17

Five (5) ( of a culture medium containing 39.5 % of sucrose and 5.3 % of corn steep liquor were loaded into a fermenter of 7 l in volume, and were added with 300 ppm of a defoamer, followed by steam sterilization at 120° C. for 20 minites. After cooling, the culture medium was adjusted to pH 4.1 with caustic soda. Added to this medium was thereafter 300 m( of a seed culture solution of *Aureobasidium* sp. SN-G42 strain (FERM BP-1430) prepared with the same medium as the aforesaid medium in accordance with the procedures of Example 7. Culture was then carried out at 35° C. and 500 rpm under an aeration of 0.25 vvm for 6 days.

After the completion of culture, the analysis of the culture solution indicated that the sucrose was entirely consumed, and the yeilds of erythritol and glycerol therein were 42.4 % and 5.8 %, respectively.

Example 18

Five (5) l of a culture medium containing 45.0 of sucrose and 6.0 % of corn steep liquor were loaded into a fermenter of 7 ( in volume, and were added with 300 ppm of a defoamer, followed by steam sterilization at 120° C. for 20 minutes. After cooling, the culture medium was adjusted to pH 4.1 with caustic soda. Added to this medium was thereafter 300 ml of a seed culture solution of *Aureobasidium* sp. SN-G42 strain (FERM BP-1430) prepared with the same medium as the aforesaid medium in accordance with the procedures of Example 7. Culture was then carried out at 35° C. and 500 rpm under an aeration of 0.25 vvm for 6 days.

After the completion of culture, the analysis of the culture solution indicated that the sucrose was entirely consumed, and the yields of erythritol and glycerol therein were 41.7 % and 3.8 %, respectively.

Example 19 (Preparation of Mutants)

Five (5) ml of a liquid culture medium containing 22.0 % of glucose and 0.5 % of yeast extract were inoculated with *Aureobasidium* sp. SN-124A strain (FERM BP-1429) for 2-day rotary shaking culture at 30° C., thereby obtaining a cultured product.

Then, the thus cultured product was diluted 100 times with a 22.0 % glucose solution, and was irradiated with an ultraviolet lamp of 15 W (Toshiba Sterilizer lamp GL 15) from a distance of 30 cm for 40 minutes, while stirred in a petri dish.

After the irradiation, the thus treated solution in the petri dish was applied over an agar culture medium containing 22.0 % of glucose, 0.5 % of yeast extract and 1.5 % of agar, and stationary culture was carried out at 30° C. for 4 days to pick up grown strains.

Then, the thus picked-up strains were inoculated on a liquid culture medium containing 22.0 % of glucose and 0.5 % of yeast extract for 2-day rotary shaking culture at 30° C, thereby obtaining a cultured product.

Then, this cultured product was diluted in a manner similar to the aforesaid manner, and was thereafter re-irradiated with ultraviolet rays for 20 minutes under the same conditions as mentioned above.

After the irradiation, the thus treated solution was applied over an agar culture medium containing 33.5 % of glucose, 1.0 % of yeast extract and 1.5 % of agar, and stationary culture was carried out at 30° C. for 4 days to pick up grown strains.

Further, the thus picked-up strains were inoculated on a liquid culture medium containing 33.5 % of glucose and 1.0 % of yeast extract, and rotary shaking culture was carried out at 30° C. for 2 days to obtain a cultured product.

Next, the cells were centrifuged out of the thus obtained culture product, and were further washed twice with a 0.2 M acetic acid buffer solution (pH 5.0) containing 2 M of glucose. Afterwards, the cells were suspended in a buffer solution at a concentration of $1 \times 10^7$ cells/m(, and were treated with N-methyl-N'-nitro-N-nitrosoguanidine having a concentration of 1 mg/ml at 30° C. for 30 minutes.

After the completion of the treatment, the cells were separated in the conventional manner, and were further washed with a buffer solution. Thereafter, the cells were applied over an agar culture medium containing 40.0 % of glucose, 1.0 % of yeast extract and 1.5 % of agar, and stationary culture was carried out at 30° C. for 5 days to pick up grown strains.

The thus picked-up strains were inoculated on a liquid culture medium comprising 1.6 % of yeast extract and 40.0 % of glucose, and shaking culture was carried out at 30° C. for 2 days to obtain a cultured product. Then, the obtained culture product was diluted to $1 \times 10^7$ cells/m(, and 3 m( of the diluted product were put in a glass test tube, which was irradiated with 200 kRad of gamma ryas (60Co) from a distance of 18 cm.

After the completion of irradiation, the treated cells were applied over an agar culture medium containing 45.0 % of glucose, 1.6 % of yeast extract and 1.5 % of agar, and stationary culture was carried out at 30° C. for 5 days to pick up grown cells, thereby obtaining mutants, viz., *Aureobasidium* sp. SN-γ96 strain (FERM P-9400, FERM BP-1431).

Example 20

(a) Preparation of Seed Culture Solution

*Aureobasidium* sp. SN-γ96 strain (FERM BP-1431) were applied over a slant culture medium comprising 40.0 % of glucose, 1.6 % of yeast extract and 1.5 % of agar for 5-day stationary culture at 35° C.

One platinum loop of the aforesaid slant-cultured cells were transplanted into a 500-ml conical flask, in which 100 m( of a liquid culture medium (pH 4.9) containing 40.0 % of glucose and 1.6 % of yeast extract was loaded, for 3-day culture at 35° C. Further, 9 ml of this culture solution was inoculated into a 500 ml conical flask in which 150 ml of a liquid culture medium similar to the aforesaid one was put, rotary shaking culture was carried out at 35° C. for 3 days to obtain a cultured product.

(b) Main Culture

Fifteen (15) l of a liquid culture medium containing 40.0 % of glucose and 6.8 % of corn steep liquor (which had separately been sterilized) were loaded in a fermenter having a volume of 30 l, added with 300 ppm of a defoamer ("Adecanol LG-109 manufactured by Asahi Denka K.K.), and were adjusted to pH 4.2 with sodium hydroxide. Added to this were 900 ml of the seed culture solution of *Aureobasidium* sp. SN-γ96 strain (FERM BP-1431) prepared in the aforesaid step (a). Culture was then carried out at 35° C. and 400 rpm under an aeration of 1.0 vvm for 4 days.

After the completion of culture, the analysis of the culture solution by HPLC indicated that the glucose was completely consumed, and the erythritol and glycerol contents were 18.9 % (the yield : 47.3 %) and 3.5 % (the yield : 8.8 %), respectively.

Then, the cells were centrifuged out of 600 ml of this culture solution, which was in turn decolored with activated charcoal and desalted with an ion exchange resin (IRA-140 : IR-120 =2 : 1). Subsequently, the resulting liquid was concentrated to a sugar concentration of at least 50 %, and was slowly cooled to precipitate and separate crystals. Further, the crystals were recrystallized from water to obtain polyhedral white crystals which had a melting point of 121.0° C. and were of a comfortable sweet taste. The white crystals were further indentified as erythritol (mesoerythritol) by liquid chromatography and gas chromatography as well as the measurement of the optical rotation and nuclear magnetic resonance spectra.

Example 21

Fifteen (15) l of a liquid culture medium containing 50.0 % of glucose and 6.8 % of corn steep liquor (which had separately been sterilized) were loaded in a fermenter having a volume of 30 l, added with 300 ppm of a defoamer, and were adjusted to pH 4.2 with sodium hydroxide. Added to this were 900 ml of the seed culture solution of *Aureobasidium* sp. SN-γ96 strain (FERM BP-1431) prepared in accordance with the procedures of Example 20(a). Culture was then carried out at 35° C. and 400 rpm under an aeration of 1.5 vvm for 6 days.

After the completion of culture, the analysis of the culture solution indicated that the glucose was completely consumed, and the erythritol and glycerol contents were 23.3 % (the yield: 46.5 %) and 4.5 % (the yield : 9.0 %), respectively.

Example 22

Two (2) ( of a liquid culture medium containing 60.2 % of glucose and 2.0 % of yeast extract (which had separately been sterilized) were loaded in a fermenter having a volume of 3 l, and added with 200 ppm of a defoamer. Added to this were 80 m( of the seed culture solution of *Aureobasidium* sp. SN-γ96 strain (FERM BP-1431) prepared in accordance with the procedures of Example 20(a). Culture was then carried out at 35° C. and 1000 rpm under an aeration of 2.5 vvm for 7 days.

After the completion of culture, the analysis of the culture solution indicated that the glucose was completely consumed, and the erythritol and glycerol contents were 28.8 % (the yield : 47.7 %) and 6.8 % (the yield : 11.3 %), respectively.

Example 23

Two (2) l of a liquid culture medium containing 75.5 % of glucose and 2.0 % of yeast extract (which had separately been sterilized) were loaded in a fermenter having a volume of 3 (, and added with 200 ppm of a defoamer. Added to this were 80 m( of the seed culture solution of *Aureobasidium* sp. SN-γ96 strain (FERM BP-1431) prepared in accordance with the procedures of Example 20(*a*). Culture was then carried out at 35° C. and 1000 rpm under an aeration of 2.0 vvm for 11 days.

After the completion of culture, the analysis of the culture solution indicated that the glucose was completely consumed, and the erythritol and clycerol contents were 24.5 % (the yield : 32.4 %) and 11.0 % (the yield : 14.3 %), respectively.

Example 24

Five (5) ( of a liquid culture medium containing 50.0 % of sucrose and 6.8 % of corn steep liquor (which had separately been sterilized) were loaded in a fermenter having a volume of 7 l, added with 300 ppm of a defoamer, and were adjusted to pH 4.2 with sodium hydroxide. Added to this were 300 m( of the seed culture solution of *Aureobacidium* sp. SN-γ96 strain (FERM BP-1431) prepared in accordance with the procedures of Example 20(*a*). Culture was then carried out at 35° C. and 800 rpm under an aeration of 1.0 vvm for 5 days.

After the completion of culture, the analysis of the culture solution indicated that the sucrose was completely consumed, and the erythritol and glycerol contents were 23.6 % (the conversion ratio : 47.25 %) and 5.0 % (the conversion ratio : 10.0 %), respectively.

Example 25

Two (2) l of a liquid culture medium containing 61.0 % of sucrose and 2.0 % of corn steep liquor (which had separately been sterilized) were loaded in a fermenter having a volume of 3 (, and added with 200 ppm of a defoamer. Added to this were 80 ml of the seed culture solution of *Aureobasidium* sp. SN-γ96 strain (FERM BP-1431) prepared in accordance with the procedures of Example 20(*a*). Culture was then carried out at 35° C. and 100 rpm under an aeration of 2.5 vvm for 6 days.

After the completion of culture, the analysis of the culture solution indicated that the sucrose was completely consumed, and the erythritol and glycerol contents were 24.6 % ( the yield : 40.3 %) and 7.8 % (the yield: 12.8 %), respectively.

Example 26

Two (2) ( of a liquid culture medium containing 93.9 % of sucrose and 2.0 % of yeast extract (which had separately been sterilized) were loaded in a fermenter having a volume of 3 l, and added with 200 ppm of a defoamer. Added to this were 80 ml of the seed culture solution of *Aureobasidium* sp. SN-γ96 strain (FERM BP-1431) prepared in accordance with the procedures of Example 20(*a*). Culture was then carried out at 35° C. and 1000 rpm under an aeration of 2.0 vvm for 15 days.

After the completion of culture, the analysis of the culture solution indicated that the sucrose was completely consumed, and the erythritol and glycerol contents were 21.6 % (the yield : 23.0 %) and 4.9 % (the yield : 5.3 %), respectively.

Example 27

Shown in this example are the results of comparison of the resistance to sugars of the wild *Aureobasidium* sp. SN-124A strains of the present invention and their mutants *Aureobasidium* sp. SN-G42 strains and *Aureosbasidium* sp. SN-γ96 strains. *Procedures*

One hundred (100) m( of each of liquid culture media containing 2.0 % of yeast extract (manufactured by Difco, Co., Ltd.) and given amounts (22.0 to 83.3 %) of glucose were loaded into a conical flask of 500 ml in volume, and were sterilized in the conventional manner. Thereafter, the slant-cultured cells of *Aureobasidium* sp. SN-124A, SN-G42 and SN-γ96 strains were inoculated on the respective media for seed culture at 35° C. for 1 to 5 days.

Next, 2 l of each liquid culture media containing given amounts (22.0 to 83.3 %) of glucose and 20 % of yeast extract were put in a fermenter of 3 l in volume. Added to the medium were 80 m( of each of the aforesaid seed culture solutions having the corresponding substrate concentrations. Culture was then carried out at a culture temperature of 35° C. and at 1000 rpm under an aeration of 2.0 vvm until the glucose in each medium was completely consumed (for 2 to 14 days).

After the completion of culture, the amount of erythritol contained in each culture solution was measured by HPLC.

Results

The yields of erythritol per consumed glucose are tabulated as follows:

| Glucose Concentration in % | Yields of Erythritol in % | | |
|---|---|---|---|
| | Parent Strains (SN-124A) | Mutents (SN-G42) | Mutents (SN-γ96) |
| 22.0 | 41.5 | 50.6 | 48.2 |
| 33.5 | 37.0 | 48.0 | 45.9 |
| 39.5 | 29.7 | 46.8 | 47.5 |
| 45.0 | 16.2 | 43.5 | 45.3 |
| 53.3 | — | 40.5 | 42.5 |
| 60.2 | — | 32.4 | 43.1 |
| 67.9 | — | — | 38.6 |
| 75.5 | — | — | 32.4 |
| 83.3 | — | — | 26.4 |

Example 28

Shown in this example are the results of comparison of the foaming, flocculation and hydrophilic natures of *Aureobasidium* sp. SN-124A strain and their mutants, *Aureobasidium* sp. SN-G42 strain and SN-γ96 strain.

Procedures

Five (5) ml of a liquid culture medium containing 1.0 % of yeast extract and 33.5 % of glucose were put into a test tube, and were steam-sterilized at 120° C. for 15 minutes. After cooling, the medium was adjusted to ph 5.5, and was inoculated with the slant-cultured cells of *Aureobasidium* sp. SN-124A strain or SN-G42 strain, followed by rotary shaking culture at 30° C. for 5 days. After the completion of culture, the culture solution was kept stationary for 15 minutes to observe the generation of foams and the state of flocculation of the cells (foaming and flocculation natures).

Subsequently, an equal amount of benzene was added under vigorous agitation to the culture solution, and the resulting solution was thereafter kept stationary for about 30 minutes to observe the transfer of the cells into the benzene phase (hydrophilic nature).

Similar observations were also carried out with *Aureobasidium* sp. SN-γ96 strains on a liquid culture containing 1.6 % of yeast extract and 40.0 % of glucose.

Results

When the parent *Aureobasidium* sp. SN124A strain was aerobically cultured on a liquid culture medium, marked foaming occurred. The foams remained for a longer period of time even after the stopping of reciprocal shaking. The cells in the culture solution were flocculated immediately upon stirring being interrupted, thus giving sediments.

However, even when the mutants, *Aureobasidium* sp. SN-G42 and SN-γ96 strains were cultured under the same conditions as mentioned above, no foaming was observed. Nor did the flocculation of the cells occur, even after the stopping of reciprocal shaking.

Further, when suitable amounts of benzene were added to the respective culture solutions of the parent strains and mutants to form double-phase systems, it was found that the cells of the parent strains were passed into the benzene phase without leaving no trace in the aqueous phase, but the cells of the mutants were all kept in the aqueous phases without passing into the benzene phases.

What is claimed is:

1. A method for preparing erythritol by fermentation of sugar, which comprises inoculating artificial mutant of *Aureobasidium* sp. SN-124A strain (FERM BP-1429) on a liquid culture medium of pH 4 to 9 containing an assimilable carbon source in an amount of at least 30 % and an assimilable nitrogen source, and aerobically culturing them at a temperature of 30° to 38° C. to form and accumulate erythritol in said culture medium for collection.

2. The method as defined in claim 1, in which said artificial mutant of *Aureobasidium* sp. SN-124A strain is *Aureobasidium* sp.SN-G42 strain (FERM BP-1430).

3. The method as defined in claim 1, in which said artificial mutant of *Aureobasidium* sp. SN-124A strain is *Aureobasdium* sp. SN-γ96 strain (FERM BP-1431).

4. The method as defined in claim 2, wherein the sugar concentration is 40% to 55%.

5. The method as defined in claim 4, wherein the sugar concentration exceeds 40%.

6. The method as defined in claim 3, wherein the sugar concentration is 20% to 95%.

7. The method as defined in claim 3, wherein the sugar concentration exceeds 40%.

8. A method for preparing erythritol by fermentation of sugars having a total concentration in the range of 20% to 95%, which comprises inoculating strain selected from the group of consisting of *Aureobasidium* sp. SN-124A strain (FERM BP-1429) and mutants thereof on a liquid culture medium of pH 4 to 9 containing an assimilable carbon source and an assimilable nitrogen source, and aerobically culturing said microorganism at a temperature of 30 ° to 38° C. to form and accumulate erythritol in said culture medium for collection.

* * * * *